(12) United States Patent
Behan et al.

(10) Patent No.: US 6,660,288 B1
(45) Date of Patent: Dec. 9, 2003

(54) INSECT REPELLENTS

(75) Inventors: John Martin Behan, Kent (GB); Richard Arthur Birch, Kent (GB)

(73) Assignee: Quest International B.V., Naarden (NL)

( * ) Notice: Subject to any disclaimer, the term of this patent is extended or adjusted under 35 U.S.C. 154(b) by 0 days.

(21) Appl. No.: 09/806,773

(22) PCT Filed: Sep. 17, 1999

(86) PCT No.: PCT/GB99/03107

§ 371 (c)(1),
(2), (4) Date: May 29, 2001

(87) PCT Pub. No.: WO00/19822

PCT Pub. Date: Apr. 13, 2000

(30) Foreign Application Priority Data

Oct. 6, 1998 (GB) ............................................. 9821693

(51) Int. Cl.[7] ............................................. A01N 25/02
(52) U.S. Cl. ........................... 424/405; 424/43; 424/47; 424/59; 424/65; 424/69; 424/70.1; 424/26.2; 424/DIG. 10; 514/460; 514/532; 514/617; 514/675; 514/690; 514/692; 514/693; 514/699; 514/715; 514/717; 514/718; 514/750; 514/763; 514/766; 514/919; 510/101
(58) Field of Search ................................ 424/405, 401, 424/DIG. 10, 406, 195.18, 750, 770; 514/919, 675, 690, 692, 533, 766, 617, 763, 532, 460, 676, 715, 717, 718, 693, 699

(56) References Cited

U.S. PATENT DOCUMENTS

| | | | | |
|---|---|---|---|---|
| 5,143,900 A | * | 9/1992 | Steltenkamp et al. | 512/26 |
| 5,645,845 A | * | 7/1997 | Neumann et al. | 424/405 |
| 5,849,685 A | * | 12/1998 | Palmer | 372/9 |
| 6,111,055 A | * | 8/2000 | Berger et al. | 528/310 |

FOREIGN PATENT DOCUMENTS

WO   WO 96/08147   3/1996

OTHER PUBLICATIONS

Chemical Abstracts, vol. 123, No. 7, Aug. 14, 1995, Columbus, Ohio, US; abstract No. 77176, Shimizu, Tomomitsu et al: "Insect repellent for protecting textile materials" XP002126031, abstract 7 JP 07 112907 A (St Chemical Co Ltd, Japan) May 2, 1995.

Database WPI, Derwent Publications Ltd., London, GB; AN 1998–266958 XP002126034 St Kagaku KK: "Moth proofing agent–comprises terpene type compounds and paradichlorobenzene. naphtalene or pyrethroid compounds" abstract & JP 10 087407 A, 4/97.

Chemical Abstracts, vol. 110, No. 9, Feb. 27, 1989, Columbus, Ohio, US; abstract No. 71150, Okada, Isao: "Cockroach repellents containing 1–propenylbenzenes" XP002126032 abstract & JP 63 188603 A (Hasegawa, T., Co., Ltd., Japan Aug. 4, 1988.

Chemical Abstracts, vol. 130, No. 7, Feb. 15, 1999, Columbus, Ohio, US; abstract No. 77454, Ngoh, Shay P. et al: "Insecticidal and repellent properties of nine volatile constituents of essential oils against the American cockroach, *Periplaneta americana* (L)" XP002126033 abstract 7 Pestic. Sci (1998), 54(3), 261–268.

DataBase WPI, Derwent Publications Ltd., London, GB; AN 1998–266960 XP002126035 Fujii M.: "Repellent control composition for epidermic mites–containing one or more of a wide range of active components" abstract 7 JP 10 087409 A, 4/98.

* cited by examiner

*Primary Examiner*—Neil S. Levy
(74) *Attorney, Agent, or Firm*—Morgan, Lewis & Bockius LLP

(57) ABSTRACT

The use of specific perfume ingredients, e.g. tricyclodecenyl allyl ether, to repel insects. The perfume ingredients may be used in a composition comprising from 0.1 to 40 percent by weight of one or more of the perfume ingredients. Preferably at least one of the perfume ingredients has a hydrophobicity such that the common logarithm of the octanol-water partition coefficient, log P, of the perfume ingredient is in the range 1.0 to 6.0.

9 Claims, 1 Drawing Sheet

INSECT REPELLENTS

Figure 1:
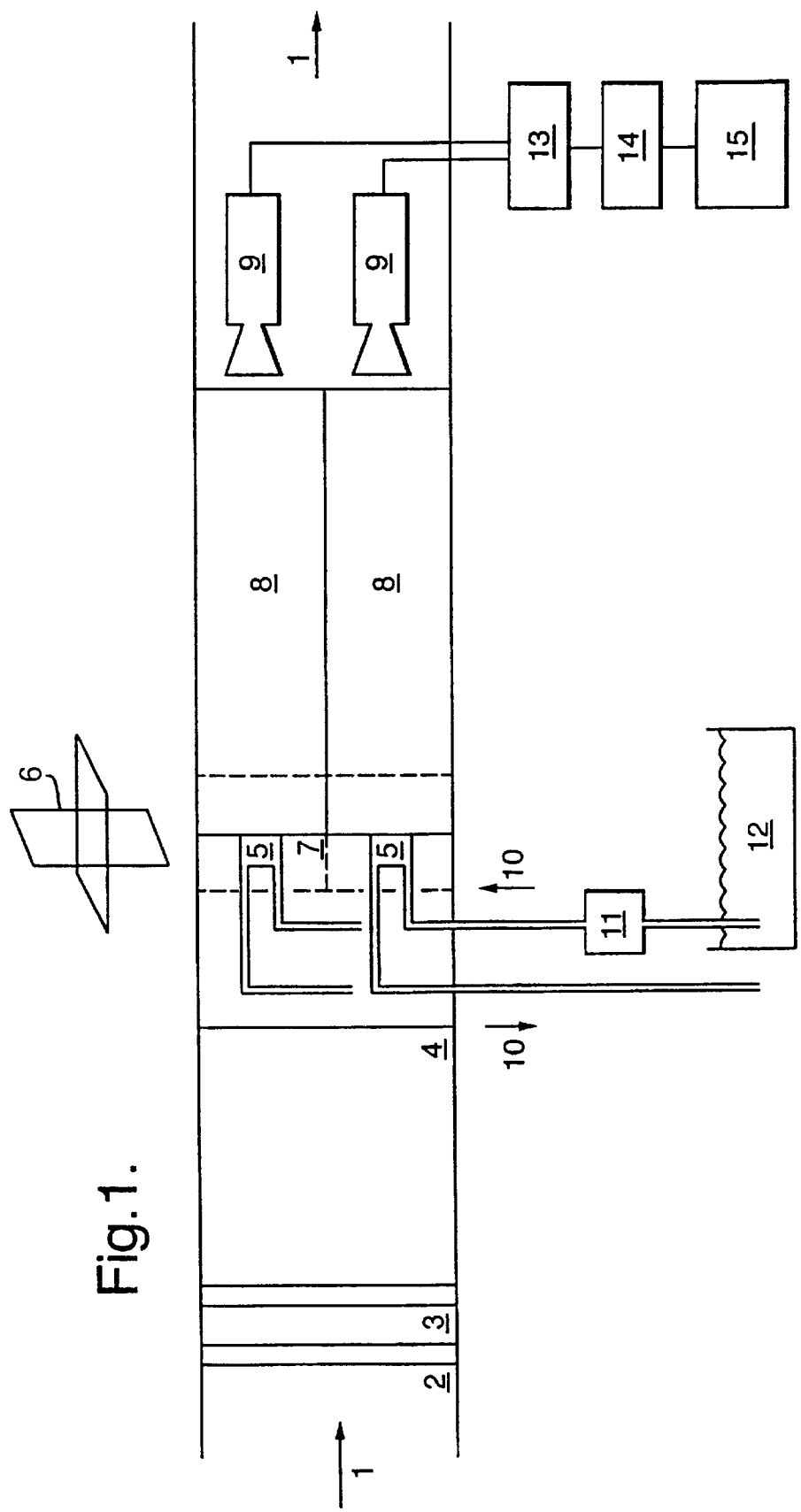

This application is the National Phase of International Application PCT/GB99/03107 filed Sep. 17, 1999 which designated the U.S. and that International Application was published under PCT Article 21(2) in English.

FIELD OF INVENTION

The present invention relates to the use of certain perfume ingredients as an insect repellent, to compositions containing the perfume ingredients and to a method of repelling insects.

BACKGROUND

Insects have long been known as a nuisance and, for some insect genera, as a health hazard. Mosquitoes, for instance, are a proven vector of diseases, and the genus Aedes in particular is associated with yellow fever, dengue, encephalitis and malaria (Encyclopaedia Britannica). Although the problems may be reduced at source with the use of DDT and other chemical sprays in the breeding areas, fears over the persistence of chlorchemicals combined with increasing mosquito resistance to control chemicals (e.g. insecticides) have led to a reappraisal of the magnitude of the nuisance and the hazard. Physical barriers to the insects are not always possible, e.g. in the open air, where some form of personal repellent is necessary.

It is also a feature of recent times that the more environmentally-aware public tend to question the safety of many chemicals which were formerly taken for granted. One of these is the well-known personal insect repellent N,N-diethyl-m-toluamide (abbreviated as DEET, and commercially available as Delphone™). This was originally seen as the natural successor to the parent molecule, N,N-diethylbenzamide which was found to be strongly insect repellent but also irritating to human skin (McCabe et al., (1954), J. Org Chem. 19, 493–498). Fears over possible allergenicity, disclosed in European Patent Application EP-A-0 167 266 (Angus Chemical Company), as well as aversion to some of the physical properties of this compound such as oiliness and odour, have led to the search for less hazardous and more aesthetically acceptable methods of repelling insect pests, particularly mosquitoes.

REVIEW OF THE PRIOR ART

Certain compounds have long been known to possess insect deterrent properties, some of this information coming from what might be termed "folk knowledge". These materials include widely-known substances such as Citronella, Tolu and Peru Balsams, Eucalyptus oils, Huon Pine and other similar oils [M. Bouvier, International Frag. Co-ord. 29 October 1976]. Other materials known for their deterrent properties include those having camphoraceous odours, such as Camphor itself, Cypress oils, Galbanum etc. [H&R Contact, 36, 1984].

Perfume ingredients with insect repellent properties used either alone, or in a perfume composition, and/or in some form of carrier or base overcome many of the problems highlighted above. Many common types of household insects such as American cockroaches (*periplaneta americana*) are classified as pests and significant effort has been made to control or eradicate them. A variety of chemicals that are effective in repelling cockroaches has been discovered. These chemicals are used in the household by applying or spraying them to surfaces of walls, floors, cabinets, containers, rugs, upholstery and carpeting, and in potential nesting places for insects, such as inside walls and between floors. They have been used together with hardsurface cleaners (EP-A-0 619 363) and wax floor polishes (U.S. Pat. No. 3,018,217).

It is known in the art that organic materials and essential oils can be repellent against insects. In the art this has been measured in a variety of ways with different insects. The majority of the prior art has been directed towards mosquitoes and in particular the species *aedes aegyptii*. The results of these studies has led to a list of preferred materials. Surprisingly we have found that additional perfume ingredients, preferably when used above certain limits in perfume compositions can lead to enhanced insect repellency.

PCT Application WO 96/08147 discloses the use of a number of different compounds as insect repellents and also a method by which the repellency of compounds to insects can be reliably tested.

SUMMARY OF THE INVENTION

It has now been surprisingly found that a number of perfume ingredients are effective insect repellents.

Accordingly, the present invention provides the use of at least one perfume ingredient selected from the group consisting of Citral diethyl acetal (Citrathal*), Tricyclodecenyl allyl ether (also known as 8-(allyloxy) tricyco [$5.2.1.0.^{2.6}$ ]dec-3-ene) [Fleuroxene*], 2-(2-methylpropyl )-4-hydroxy4-methyltetrahydropyran [Florosa*], N-methyl-N-phenyl-2-methylbutanamide [Gardamide*], 4-isobutyrate-3-methoxybenzaldehyde [Isobutavan*], 1-hydroxy-2-methoxy4-propenylbenzene [Isoeugenol*], 2,2,7,7-tetramethyltricyclo[$6.2.1.0^{1.6}$]undecan-5-one [Isolongifolanone*], 7-formyl-5-isopropyl-2-methylbicyclo[2.2.2]oct-2-ene [Maceal*], 3-methyl-5-phenyl-1-pentanal [Mefranal*], alpha iso methyl ionone (also known as 4-(2,6,6-trimethyl-2-cyclohexen-1 -yl)-3-methyl-3-buten-2-one), myrcenyl acetate (also known as 2-methyl-6-methylene-7-octen-2-yl acetate) [Neobergamate*], 10-isopropyl-2,7-dimethyloxaspiro [4.5] 3,6-decadiene [Neocaspirene*], tricyclo[$5.2.1.0^{2.6}$]dec4-en-8-yl 2,2-dimethylpropanoate (Pivacyclene*), 2-phenylethyl pivalate (also known as phenylethyl-2,2-dimethylpropanoate) [Pivarose*]

and 2,4-dimethyl-4-phenyltetrahydrofuran [Rhubafuran*] as an insect repellent. (*trade marks)

In another aspect, the invention provides a method of repelling insects from an object or an airspace, comprising application to the object or into the airspace, of an effective amount of at least one perfume ingredient selected from the group consisting of the aforementioned perfume ingredients. Typically, the object is a human body or a solid surface such as a wall or floor.

The perfume ingredients from the aforementioned list which are more effective as insect repellents are those which have an octanol-water partition coefficient such that "log P" has a value in the range from 1.0 to 6.0, more preferably 2.0 to 5.0, and particularly 2.5 to 4.5. "log P" is the common logarithm of the octanol-water partition coefficient and is well known in the literature as an indicator of hydrophobicity and water solubility (see Hansch and Leo, Chemical Reviews, 526 to 616 (1971), 71 and Hansch, Quinlan and Lawrence J. Organic Chemistry, 347 to 350 (1968), 33). Where such values are not available in the literature they may be measured directly or approximately estimated using mathematical algorithms. Software providing such estimates is available commercially, for example 'LogP' from Advanced Chemistry Design Inc.

In addition, those perfume ingredients which are more effective as insect repellents have a "Kovats" index value in the range from 1150 to 1650, more preferably 1250 to 1600, and particularly 1300 to 1560. Kovats indices are calculated from the retention time in a gas chromatographic measurement referenced to the retention time for alkanes (see Kovats, Helv. Chim. Acta 41, 1915 (1958)). Indices based on the use of a non-polar stationary phase have been used in the perfumery industry for some years as a descriptor relating to the molecular size and boiling point of ingredients. A review of Kovats indices in the perfume industry is given by T Shibamoto in "Capillary Gas Chromatography in Essential Oil Analysis", P Sandra and C Bicchi (editors), Huethig (1987), pages 259 to 274. A common non-polar phase which is suitable is 100% dimethyl polysiloxane, as supplied, for example, under a variety of trade names such as HP-1 (Hewlett Packard), CP Sil 5 CB (Chrompak), OV-1 (Ohio Valley) and Rtx-1 (Restek).

A further property of the aforementioned perfume ingredients which confers good performance as an insect repellent is a capability of forming hydrogen bonds of greater than 60 on the Koppel Pal'm scale (J. Chem. Soc. Perkin Trans. 2, 1976, pp 1628).

The insect repellent perfume ingredients described herein are preferably used in a composition, more preferably in a perfume composition, preferably at a concentration of at least 10%, more preferably at least 30%, and particularly at least 50% by weight. The composition used in the invention comprises at least one, and, more preferably, 3 or 4 of the perfume ingredients described herein. The individual perfume ingredients are preferably present at a concentration in the range from 0.1% to 40%, more preferably, 0.5% to 20% by weight. The perfume composition may contain other known insect repellents, preferably of previously known insect repellent perfume ingredients, preferably at a concentration of at least 10%, more preferably at least 30%, and particularly at least 50% by weight.

Compositions containing more than one of the aforementioned insect repellent perfume ingredients preferably contain at least one such perfume ingredient having a "log P" value in the range 1.0 to 6.0 or at least one such perfume ingredient having a Kovats index in the range 1150 to 1650, as hereinbefore defined, or at least one such perfume ingredient capable of forming hydrogen bonds of greater than 60 on the Koppel Pal'm scale.

Preferably, the perfume ingredients described herein are used to repel insects, such as mosquitoes, particularly members of the genus Aedes and cockroaches.

Compositions used in accordance with the invention preferably constitute, or comprise, personal products or cosmetics for use on the skin and/or hair. Examples of such products include fine fragrances, colognes, skin creams, skin lotions, deodorants, talcs, bath oils, soaps, shampoos, hair conditioners and styling agents.

Alternatively, compositions used in accordance with the invention may constitute, or be comprised in, household products such as: air fresheners (including "heated" air fresheners in which insect repellent substances are released upon heating, e.g. electrically, or by burning [e.g. joss-sticks, candles]); hard surface cleaners; or laundry products (e.g. laundry detergent-containing compositions, conditioners).

Preferably the cosmetics, personal products and household products defined above comprise between 0.1% and 20%, more preferably 0.2% to 10% by weight of a composition used in accordance with the invention.

The compositions used in the invention may comprise additional materials to produce desired products such as pleasing perfumes with useful repellent activity. Other materials which may be present in the compositions (at concentrations from 0 to 99.95% w/w) include fragrances, solvents, diluents and fixatives known in the art, such as:

Aldehyde C11 (Undecylenic Aldehyde); Aldehyde iso C11 (GIV); Allspice oil; Allyl cyclohexyl propionate; Amyl salicylate; Amylcinnamic aldehyde; Anethole; Anisic alcohol; Anisic aldehyde; Applinal (Q); Bay oil; Benzyl acetate; Benzyl benzoate; Benzyl cinnamate; Benzyl propionate; Benzyl salicylate; Bourgeonal (Q); Brahmanol; Camphor powder synthetic; Cedarwood Virginian; Cedrenol; Cedryl acetate; Celestolide (IFF); Cineole; Cinnamic alcohol; cinnamic aldehyde; Cinnamon Leaf Oil: Cinnamyl acetate; cis-3-Hexenol; Citral; Citronella oil; Citronellal; Citronellol; Citronellyl acetate; Citronellyl oxyacetaldehyde; Clove oil; Coriander oil; Coumarin; Cuminic aldehyde; Cyclamen aldehyde; Decanal; 9-Decenol; Dibenzyl ether; Dibutyl phthalate; Diethyl Phthalate; Dihydromyrcenol; Dimethyl anthranilate; Dimethyl phthalate; Dimycretol (IFF); diphenylmethane; Diphenyl oxide; Dimethyl benzyl carbinyl acetate; Dodecanol; Dodecanal; Elemi oil; Ethyl methyl phenyl glycidate; Ethyl cinnamate; Ethyl safranate (Q); ethyl vanillin; Eugenol; Evergreen oils (Pine oils etc.); gamma-Nonalactone; gamma-undecalactone; Geraniol; Geranium bourbon; Geranyl acetate; Geranyl formate; Gum Benzoin; Heliotropin; Hercolyn D (HER); Hexyl benzoate; Hexylcinnamic aldehyde; Hydratropic aldehyde dimethyl acetal; Hydroxycitronellal; Hydroxycitronellal dimethyl acetal; Indole; iso Bornyl acetate; Isopropyl myristate; Iso-cyclocitral (GIV, IFF); Jasmacyclene; Jasmin oil; Lavandin Abrialis; Lavender oil; Lilial (GIV); Linalol; Linalyl acetate; Menthol Laevo; Methyl anthranilate; Methyl cedryl ketone; Methyl dihydrojasmonate; Methyl ionone; Methyl myristate; Methyl naphthyl ketone; Methyl salicylate; Moss treemoss; Musk ketone; Nerol; Nerolin Bromelia; Neryl acetate; Nonanal; Oakmoss absolute; Octanol Olibanum resionoid; para-Cresyl phenylacetate; para-Methoxyacet6phenone; Patchouli oil; Peppermint oil; Petitgrain oil; 2-Phenoxyethanol; Phenoxyethyl iso butyrate; Phenylethylacetate; Phenyethyl alcohol; Phenylethyl butyrate; Phenylethyl phenylacetate; Pimento oil; Pinene, alpha; Para-tert. butyl-cyclohexyl acetate; Resinoid Benzoin Siam; Rose oil; Rosemary oil; Sandalwood oil; terpineol; Tetrahydrolinalol; Tetrahydromuguol (IFF); Thyme Red; Undecanal; Vanillin; Verbena oil; Vetyvert Bourbon; Yara and Ylang ylang.

Compounds are obtainable from the suppliers as indicated below: for those compounds labelled "(Q)",—Quest International, "(IFF)"—International Flavours & Fragrances, Inc., "(GIV)"—Givaudan, "(HER)"—Hercules B.V.

Other active and non-active materials may be present, such as:

acidic mucopolysaccharides and their salts, Aesculus hipocastanum, aloe barbadenisis Mil (Aloe Vera Linne), α-hydroxycarboxylic acids, α-ketocarboxylic acids, amide derivatives, amino acids, amphiphilic cyclodextrin derivatives, β-sitosterol, carboxy vinyl polymer water soluble salts, carboxymethyl cellulose, carrageenan, chitin, chitosan, cholesterol, cholesterol fatty acid ester, collagen, dicarboxylic acid monostearyl esters, di-fatty acid glycerol esters, digalactosyl diglyceride, ersterol, ethanol, extract of Swertia japonica Makino, fatty acids, fatty acid citrate esters, fatty alcohols, ginseng extract, glucose esters of higher fatty acids, guar gum, gum arabic, Hamamelidaceae (Hamamelis Virginiana Witch hazel), hyaluronic acid, hydrochyloesterol, hydroxybenzoic acids, isomaltose, isopropyl alcohol, lactose, lanosterol, lipids extracted from the biomass of microorganisms, yeasts, moulds and bacteria, liposomes, locust bean gum, low molecular acidic mucopolysaccharides and their salts, low molecular weight humectant components, maltose, mineral oils, mineral powders, mono cis alkenoic acid, mucopolysaccharides, mycosterol, N-acyl lysines, N-isostearyl lysine, N-lauroyl lysine, N-myristyl lysine, N-palmitoyl lysine, N-stearoyl lysine, natrium type bentonite, natural or synthetic aminoacid with protein or peptide bonds, NMF ingredients, nonvolatile silicones, oil agents, oil matter, oligosaccharides, organic acids, pantothenic acid and its derivatives, petroleum jelly, phosphatidyl ethanolamine, phosphatidylcholine, phospholipids, polysaccharides, polyvinyl alcohol, polypeptides, proteins, raffinose, saponins, sodium hyaluronate, sources of linoleic acid, sterols, sterol esters, stigmasterol, sucrose, sugar esters of higher fatty acids, sulphatide, sunscreens, surfactants, talc, thymosterol, tocopherol, mono-, di- or tri-glycerides, vitamins and analogues, vitamin E and/or its ester compounds, volatile silicone fluids, water-soluble moisture-retaining agents, water-soluble polymers and waxes.

The perfume ingredients used in the present invention can be used as the sole insect repellent in a composition or may be used in combination with other compounds which are effective insect repellents, including previously known insect repellent perfume ingredients.

Thus, a further aspect of the invention comprises a mixture the perfume ingredients described herein with a known insect repellent. Known insect repellents which are suitable for use in a mixture with at least one perfume ingredient used in the present invention include N,N-diethyl-m-toluamide (DEET); N,N-diethylbenzamide; citronella; Tolu balsam; Peru balsam; Eucalyptus oil; Huon pine oil; camphor; cypress oil; galbanum; diethyl phthalate; dimethyl phthalate; dibutyl phthalate; 1,2,3a,4,5a,6,7,8,9,9a,9b-dodecahydro-3a,6,6,9a-tetramethyinaphtho[2,1 -b]furan; 4-(tricyclo[5.2.1.0$^{2-6}$]decylidene-8)butanal; 1-ethoxy-1-(2'-phenylethoxy)ethane; acetyl cedrene an propylidene phthalide.

A further composition according to the invention comprises a mixture of at least one of the aforementioned perfume ingredients and a further compound, said further compound being present in an amount which is sufficient to ensure that said further compound contributes to said composition an insect repellent effect equivalent to a repellency of at least 10% as determined by the insect repellency test defined in Example 1. Preferably, the further compound is present in said composition in an amount which is sufficient to ensure that said further compound contributes an insect repellent effect equivalent to a repellency of at least 20% as determined by said insect repellency test. More preferably, the insect repellent effect contributed by the further compound is equivalent to a repellency of at least 30%.

The invention is illustrated by the following non-limiting examples and by reference to FIG. 1, which is a schematic representation of an apparatus suitable for testing compounds as insect repellents.

EXAMPLE 1

Insect Repellency Test—Mosquitoes

The effectiveness of the perfume ingredients as an insect repellent was tested using an apparatus similar to that disclosed in PCT Application WO 96/08147 and illustrated in FIG. 1. The method is described for testing of citral diethyl acetal but can be adapted to test any other compound in place of citral diethyl acetal.

Four test chambers were prepared using 300 mm 200 gauge layflat tubing. The synthetic plastics tubing was attached to oblong stainless steel frames (150 mm by 150 mm by 900 mm) using double-sided adhesive tape. 200 mm squares of cotton netting were used to cover the ends of the chambers and were secured using adhesive tape.

Mosquitoes (naive insects of the species *Aedes aegypti*, 4 to 7 days old) were introduced into each chamber 8 and the chambers 8 were kept in a separate room until the test was ready to begin.

The exhaust fan which vents the room in which the test was performed was switched on.

Four targets 5 (only two shown) were prepared as follows: double layers of semi-porous membrane were stretched over the open ends of four open ended glassware bulbs (diameter of open end 43 mm) and secured using elastic bands. Testing was carried out at 27° C. The membranes were kept moist and warmed above the ambient temperature throughout the test by passing a supply of water (at 34° C.) through the glassware bulbs, so as to contact the inner surface of the membranes.

Citral diethyl acetal (30 microliters) was applied to a membrane and spread as evenly as possible across the membrane surface. This was repeated with two other membranes and the fourth membrane was left untreated as a control.

The chambers 8 containing the mosquitoes were positioned so that each chamber had one netting end pressed against one of the targets 5. Glass partitions in the form of a cross 6 were used to separate each target 5 and chamber end from its neighbour.

600 mm 200 gauge layflat tubing was used to connect the various elements as shown in FIG. 1. Air was forced by an inlet fan (not shown) over the filters 2, 3, over the targets 5, and through the test chambers containing the mosquitoes. The separation of the membranes ensured that air passing over a particular membrane would pass through only one test chamber 8.

The filters 2, 3 were used to remove volatile elements from the air passing over the mosquitoes; filter 2 contained activated charcoal and filter 3 contained a molecular sieve (Union Carbide type 5A zeolite). The material in each filter 2, 3 was held within the cells of a 25 mm thick sheet of aluminium honeycomb sandwiched between two sheets of stainless steel mesh held in an aluminium frame. The filters 2, 3 were bolted by their frames to the inside of an aluminium tunnel such that air passing along the tunnel passed through the filters 2, 3.

Four cameras 9 (only two shown) positioned downwind of the test chambers 8 were each focused onto a particular target 5, and the images produced by the cameras displayed on a single monitor 15 by means of a quad splitter 13. An electronic timer was used to project the date and time onto the screen, and the video recorder 14 was used to record the data.

The mosquitoes in the test chambers 8 were activated by introduction of a human breath stimulus upwind of the targets 5 and the number of insects attempting to bite each target 5 over the next ten minute period was recorded. After ten minutes, the recording was stopped and the test chambers 8 removed from their position immediately downwind of the targets 5.

The targets 5 were left untouched (although still warmed and moistened) for one hour with the fans switched on, after which time the test chambers 8 were re-introduced and the test repeated to determine the repellency of the citral diethyl acetal one hour after application.

The numbers of mosquitoes attempting to bite each of the targets 5 was noted every 10 seconds throughout each ten minute recording period. The 60 readings were used to produce a figure for the mean number of insects biting each target 5 during the ten minute test periods. The reading obtained for the untreated target 5 was used to give a measure of the basic avidity of the mosquitoes used in the test and this was taken into account when analysing the results.

EXAMPLE 2

Insect Repellency Test—Cockroaches

A set of ten containers was prepared, each approximately 300 mm×150 mm×100 mm. Each contained two refuges made from small plastic plant pots approximately 40 mm×40 mm×40 mm with a doorway approximately 20 mm×15 mm. The inside of one refuge was treated with gpc base (formulation below) containing the test material. The second refuge was treated with unperfumed gpc base. A small quantity of food and water was placed in each container. A single cockroach (*periplaneta americana*) was placed into each of the ten containers and the normal daily light/dark cycle followed for 24 hours. The cockroaches were of mixed age and gender. At the end of the cycle, when the lights were on, the positions of the cockroaches were noted.

- 0 or 1 cockroaches in the test refuges was classified as good repellent,
- 2 cockroaches in the test refuges was classified as moderate repellent, and
- 3 or more cockroaches in the test refuges was classified as not repellent.

If 2 or fewer cockroaches were in the test refuge and more than 2 were outside either refuge the test was repeated.

| Gpc formulation | |
|---|---|
| | Weight % |
| Dobanol 91-5 | 5.0 |
| Polyacrylic acid | 0.2 |
| Butyl digol | 3.0 |
| Sodium cumene sulphonate | 1.0 |
| Perfume ingredient | 1.0 |
| Water | 89.8 |

What is claimed is:

1. A method of repelling an insect selected from the group consisting of mosquitoes and cockroaches comprising subjecting said insect to an insect repelling amount of a composition comprising at least three perfume ingredients selected from the group consisting of tricyclodecenyl allyl ether, 2-(2-methylpropyl)-4-hydroxy-4-methyltetrahydropyran, N-methyl-N-phenyl-2-methylbutanamide, 4-isobutyrate-3-methoxybenzaldehyde, 2,2,7,7-tetramethyltricyclo [6.2.1.0$^{1.6}$]undecan-5-one, 7-formyl-5-isopropyl-2-methylbicyclo[2.2.2]oct-2-ene, 3-methyl-5-phenylpentanal, alpha iso methyl ionone, 10-isopropyl-2,7-dimethyloxaspiro [4.5]3,6-decadiene, tricyclo[5.2.1.0$^{2.6}$]dec-4-en-8-yl 2,2-dimethylpropanoate, phenylethyl pivalate and 2,4-dimethyl-4-phenyltetrahydrofuran.

2. The method of claim 1 wherein the composition compriss from 0.1 percent to 40 percent by weight of said perfume ingredients.

3. The method of claim 2 wherein at least one of the perfume ingredients in the composition has a hydrophobicity such that the common logarithm of the octanol-water partition coefficient, log P, of the perfume ingredient is in the range 1.0 to 6.0.

4. The method of claim 2 or 3 wherein at least one of the perfume ingredients in the composition has a Kovats index in the range 1150 to 1650.

5. The method of claim 2 or 3 wherein at least one of the perfume ingredients in the composition has a capability of forming hydrogen bonds of greater than 60 on the Koppel Pal'm scale.

6. The method of claim 2 wherein said composition comprises a personal product, a cosmetic or a household product.

7. The method of claim 6 wherein said composition comprises a fine fragrance, a cologne, a skin cream, a skin lotion, a deodorant, a talc, a bath oil, a soap, a shampoo, a hair conditioner, a styling agent, an air freshener, a hard surface cleaner or a laundry product.

8. The method of claim 6 or 7 wherein said personal product, cosmetic or household product contains between 0.1 per cent and 20 per cent by weight of the composition.

9. The method of claim 1 wherein the composition comprises 3 or 4 of said perfume ingredients.

* * * * *